United States Patent [19]

Lanzilotti

[11] 4,089,853

[45] May 16, 1978

[54] PROCESS FOR THE PREPARATION OF CIS-5,6-DIMETHOXY-2-METHYL-3-[2-(4-PHENYL-1-PIPERAZINYL)-ETHYL]INDOLINE

[75] Inventor: Anthony Edward Lanzilotti, Pearl River, N.Y.

[73] Assignee: American Cyanamid Company, Stamford, Conn.

[21] Appl. No.: 767,092

[22] Filed: Feb. 9, 1977

[51] Int. Cl.$^2$ ............................................. C07D 295/08
[52] U.S. Cl. .................................... 544/373; 260/690
[58] Field of Search ................................ 260/268 BC

[56] References Cited

U.S. PATENT DOCUMENTS

| 3,188,313 | 6/1965 | Archer | 260/268 BC |
| 3,751,416 | 8/1973 | Allen et al. | 260/268 BC |

OTHER PUBLICATIONS

Parnes et al., J. Org. Chem. of USSR, vol. 8 (1972) pp. 2613–2614.

Primary Examiner—Paul M. Coughlan, Jr.
Attorney, Agent, or Firm—Edward A. Conroy, Jr.

[57] ABSTRACT

There is provided a process for the manufacture of pure cis isomer of 5,6-dimethoxy-2-methyl-3-[2-(4-phenyl-1-piperazinyl)ethyl]indoline by the ionic hydrogenation of 5,6-dimethoxy-2-methyl-3-[2-(4-phenyl-1-piperazinyl)ethyl]indole.

2 Claims, No Drawings

PROCESS FOR THE PREPARATION OF CIS-5,6-DIMETHOXY-2-METHYL-3-[2-(4-PHENYL-1-PIPERAZINYL)-ETHYL]INDOLINE

BRIEF SUMMARY OF THE INVENTION

The present invention relates to a novel process for the ionic hydrogenation of 5,6-dimethoxy-2-methyl-3-[2-(4-phenyl-1-piperazinyl)ethyl]indole whereby there is obtained cis-5,6-dimethoxy-2-methyl-3-[2-(4-phenyl-1-piperazinyl)ethyl]indoline which is totally free of the trans-isomer. Cis-5,6-dimethoxy-2-methyl-3-[2-(4-phenyl-1-piperazinyl)ethyl]indoline is a known tranquilizing agent as described in U.S. Pat. Nos. 3,751,416 and 3,900,563 and may be represented by the following structural formula:

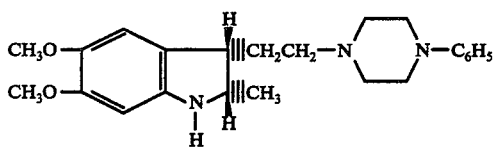

The starting material for the novel process of the present invention, 5,6-dimethoxy-2-methyl-3-[2-(4-phenyl-1-piperazinyl)ethyl]indole, is described in U.S. Pat. No. 3,188,313.

BACKGROUND OF THE INVENTION

Hydrogenation is one of the most widely used and extensively studied methods in synthetic organic chemistry. The ionic hydrogenation reaction is based on the principle that the carbonium ion, formed by protonation of a double bond, reacts with an hydride ion donor (proton and electron pair) to form the hydrogenation product as follows:

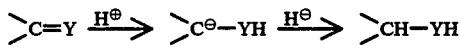

In this ionic hydrogenation reaction, the hydrogenating pair consists of a proton donor and an hydride ion donor. The hydrogenating pair must meet the following requirements. First, its components must not react with each other. Second, they should not be involved in side reactions with the substrate. Third, the hydrogenation agents and their conversion products must not hinder the evolution of the reduced compounds. In these respects, the pairs involving strong acids and organosilanes have proved most useful. As is usually the case with electrophilic addition, ionic hydrogenation is essentially accompanied by trans-addition of the proton and the hydride ion to the double bond. For example, hydrogenation of 2,3-dimethylindole results essentially in trans-2,3-dimethyl-2,3-dihydroindole, trans:cis ratio being 1.4:1 at 60° C. See Kursanov et al., *Synthesis* 9, 633 (1974).

DETAILED DESCRIPTION OF THE INVENTION

The tin and hydrochloric acid reduction of 5,6-dimethoxy-2-methyl-3-[2-(4-phenyl-1-piperazinyl)ethyl]indole to cis-5,6-dimethoxy-2-methyl-3-[2-(4-phenyl-1-piperazinyl)ethyl]indoline suffers from low productivity in that it has not been possible to isolate more than 60–65% of crude product. Furthermore, this crude material is contaminated with 6–7% of trans-isomer and 1–2% of starting material. Purification by two recrystallizations is required to provide pure cis-isomer in 9% overall yield. Alternate methods of reducing the starting indole such as electrochemical-lead electrodes, diborane and sodium methoxide, and catalytic reduction with copper chromite catalyst provide from 50/50 cis/trans mixtures to 70/30 cis/trans mixtures of indoline. The stereoselectivity of the novel process of the present invention is thus completely unexpected particularly in view of the fact that ionic hydrogenation usually results in the formation of the thermodynamically more stable trans-isomer.

Suitable proton donors which may be employed in the novel process of the present invention are concentrated phosphoric acid, concentrated sulfuric acid, polyphosphoric acid, hydrofluoric acid, trifluoroacetic acid, trichloroacetic acid, alkylsulfonic acids such as methanesulfonic acid, and arylsulfonic acids such as p-toluenesulfonic acid; or mixtures thereof. Also suitable as proton donors are solutions of concentrated sulfuric or phosphoric acid or of an arylsulfonic acid such as p-toluenesulfonic acid in glacial acetic acid. However, trifluoroacetic acid is the preferred proton donor for the novel process of the present invention. Suitable hydride ion donors which may be employed in the novel process of the present invention are di(alkyl $C_1$–$C_3$)silanes, tri(alkyl $C_1$–$C_3$)silanes, diphenylsilane, triphenylsilane, cycloheptatriene, saturated aliphatic and aromatic hydrocarbons with hydrogen at a tertiary carbon atom, adamantane, xanthene, and tropilidene. Of these, trimethylsilane and triethylsilane are the preferred hydride ion donors for the novel process of the present invention.

In practicing the novel process of this invention, one employs a large molar excess of proton donor since the proton donor also functions as the solvent for the reaction mixture. In fact, the use of any other solvent of any kind is deleterious to the ionic hydrogenation process of this invention. Hence, for every gram molecular weight of indole starting material there is employed from about 0.5 to about 2.0 kilograms of proton donor. In the event that the proton donor is not liquid, such as benzenesulfonic acid, then 2–3 moles of proton donor in glacial acetic acid per mole of indole starting material may be employed. In practicing the process of this invention, there is also employed from about 4 to about 8 gram moles of hydride ion donor per gram molecular weight of indole starting material. The reaction is usually carried out at from about 25° to about 65° C. but hydrogenation may proceed at temperatures as low as −15° C. Higher temperatures increase the reaction rate but at the same time the extent of interaction of the proton donor with the hydride ion donor also increases. In general, however, temperatures of 45°–55° C. are preferred. The reaction is generally carried out for a period of time of from about 24 hours to 72 hours or more but usually a period of about 48 hours will suffice.

The indoline product of the ionic hydrogenation of the present invention is isolated by first drowning the reaction mixture in a large excess of water. The resulting solution is then made alkaline to pH 10 with any convenient base such as caustic, soda ash, or concentrated aqueous ammonia. The resulting alkaline solution is then extracted with any water insoluble organic solvent which dissolves the indoline product such as methylene chloride, ethyl acetate, or chloroform. The extract is then concentrated in vacuo to provide crude cis-5,6-dimethoxy-2-methyl-3-[2-(4-phenyl-1-piperazinyl)-ethyl]indoline. Upon crystallization from a suitable solvent such as ethanol, isopropanol, ethyl acetate, etc., yields from 68% to 80% of pure cis-isomer may be obtained.

The invention will be described in greater detail in conjunction with the following specific examples.

EXAMPLE 1

Preparation of 5,6-Dimethoxy-2-methyl-3-[2-(4-phenyl-1-piperazinyl)ethyl]indoline by Triethylsilane/Trifluoroacetic Acid Reduction at Room Temperature A 379 mg. portion of 5,6-dimethoxy-2-methyl-3-[2-(4-phenyl-1-piperazinyl)ethyl]indole is dissolved in 4 ml. of trifluoroacetic acid by warming. The solution is cooled to room temperature and 928 mg. of triethylsilane is added. The reaction mixture is then allowed to stir for a period of 72 hours. The blue-green solution is added to about 100 ml. of an ice and water mixture and made alkaline (pH 10) with potassium hydroxide. The oily precipitate is extracted four 30 ml. portions of ethyl acetate. The combined extract is washed with two 25 ml. portions of water, dried over magnesium sulfate, and concentrated at room temperature. The resulting oily residue is dissolved in 5 ml. of isopropyl alcohol and is cooled to 0° C. After scratching to get seed, the solution is placed in a chill room overnight. The product is collected by filtration and is washed with 3 ml. of cold isopropyl alcohol followed by 15 ml. of hexane then is dried in a steam oven overnight at 60° C. to yield 260 mg. (68% yield) of 99%+ pure cis isomer, m.p. 114°–116° C.

EXAMPLE 2

Preparation of 5,6-Dimethoxy-2-methyl-3-[2-(4-phenyl-1-piperazinyl)ethyl]indoline by Triethylsilane/Trifluoroacetic Acid Reduction At Elevated Temperature A 7.3 gm. portion of 5,6-dimethoxy-2-methyl-3-[2-(4-phenyl-1-piperazinyl)ethyl]indole is dissolved in 40 ml. of trifluoroacetic acid at 55° C. with vigorous stirring, then 4.5 gm. of triethylsilane is added and the reaction mixture is allowed to stir at 55°–60° C. for a total of 48 hours. After 24 hours of this time, an additional 2.7 gm. of triethylsilane is added and the reaction is allowed to continue. The dark reddish-brown solution is concentrated in vacuo and the residue is dissolved in methylene chloride. The solution is concentrated again in vacuo and after three 50 ml. methylene chloride strippings, the residue is dissolved in 100 ml. of methylene chloride and is mixed for 4½ hours with 100 ml. of cold 2N aqueous sodium hydroxide. The methylene chloride portion is deparated and the aqueous sodium hydroxide is extracted with three 50 ml. portions of methylene chloride. The methylene chloride solutions are combined and extracted with two 25 ml. portions of 2N sodium hydroxide, then the methylene chloride is washed with four 50 ml. portions of water (until weakly basic). After drying over anhydrous sodium sulfate, the organic solvent is filtered through diatomaceous earth/activated charcoal and is concentrated in vacuo at 50° C. The residue is diluted with 50 ml. of hexane and is concentrated. Then the residue is dissolved in 50 ml. of ether and is again concentrated. Finally, this residue is dissolved in 50 ml. of isopropyl alcohol and is concentrated to give a tan solid which is dissolved in 15 ml. of hot isopropyl alcohol. This solution is allowed to cool to room temperature resulting in crystal formation. The crystal bearing liquid is placed in a refrigerator overnight. The product is collected by filtration, is washed with two 5 ml. portions of cold isopropyl alcohol and dried in vacuo at 50° C. for 4 hours to yield 5.90 gm. (80% yield) of 99%+ pure cis isomer of the product of the invention, m.p. 110°–112° C.

I claim:

1. A process for the preparation of cis-5,6-dimethoxy-2-methyl-3-[2-(4-phenyl-1-piperazinyl)ethyl]indoline which comprises ionically hydrogenating 5,6-dimethoxy-2-methyl-3-[2-(4-phenyl-1-piperazinyl)ethyl]indole with a hydrogenation pair consisting essentially of a proton donor selected from the group consisting of concentrated phosphoric acid, concentrated sulfuric acid, trifluoroacetic acid and polyphosphoric acid and a hydride ion donor selected from the group consisting of di(alkyl $C_1$-$C_3$)silanes, tri(alkyl $C_1$-$C_3$)silanes, diphenylsilane and triphenylsilane at a temperature of from about 25° to about 65° C. for a period of time sufficient for a substantial degree of $\Delta^2$-hydrogenation to occur.

2. A process according to claim 1 wherein the proton donor is trifluoroacetic acid and the hydride ion donor is trimethylsilane or triethylsilane.

* * * * *